US011998661B2

(12) United States Patent
Faleris et al.

(10) Patent No.: US 11,998,661 B2
(45) Date of Patent: Jun. 4, 2024

(54) FASCICULATED NERVE GRAFTS, METHODS OF MAKING THE SAME, AND METHODS OF TREATMENT USING THE SAME

(71) Applicant: Axogen Corporation, Alachua, FL (US)

(72) Inventors: Jennifer Faleris, Alachua, FL (US); Kasra Tajdaran, Alachua, FL (US)

(73) Assignee: Axogen Corporation, Alachua, FL (US)

(*) Notice: Subject to any disclaimer, the term of this patent is extended or adjusted under 35 U.S.C. 154(b) by 134 days.

(21) Appl. No.: 17/451,489

(22) Filed: Oct. 20, 2021

(65) Prior Publication Data

US 2022/0125995 A1 Apr. 28, 2022

Related U.S. Application Data

(60) Provisional application No. 63/104,437, filed on Oct. 22, 2020.

(51) Int. Cl.
| | |
|---|---|
| A61L 27/52 | (2006.01) |
| A61L 27/20 | (2006.01) |
| A61L 27/22 | (2006.01) |
| A61L 27/24 | (2006.01) |
| A61L 27/38 | (2006.01) |

(52) U.S. Cl.
CPC ............ *A61L 27/3878* (2013.01); *A61L 27/20* (2013.01); *A61L 27/222* (2013.01); *A61L 27/225* (2013.01); *A61L 27/227* (2013.01); *A61L 27/24* (2013.01); *A61L 27/52* (2013.01); *A61L 2430/32* (2013.01)

(58) Field of Classification Search
CPC .............................. A61L 27/24; A61L 27/3878
See application file for complete search history.

(56) References Cited

U.S. PATENT DOCUMENTS

2003/0040112 A1* 2/2003 Muir ................... A61L 27/3675
435/368

FOREIGN PATENT DOCUMENTS

| CN | 1580253 A | * | 2/2005 |
|---|---|---|---|
| CN | 1580253 A | | 2/2005 |

OTHER PUBLICATIONS

Slutsky. A Practical Approach to Nerve Grafting in the Upper Extremity (2005), Atlas of the Hand Clinics, 10, pp. 80. (Year: 2005).*
Prest et al. Nerve-specific, xenogeneic extracellular matrix hydrogel promotes recovery following peripheral nerve injury (2018), 106A, pp. 450-459. (Year: 2018).*
Qin et al. Differential temporal expression of matrix metalloproteinases following sciatic nerve crush (2016), Neural Regeneration Research, 11, pp. 1165-1171 (Year: 2016).*
Liu et al. Tissue Engineered Peripheral Nerve Graft (2005), CN1580253 (A). Espacenet English Translation. (Year: 2005).*
International Search Report and Written Opinion issued in International Application No. PCT/US2021/055937, dated Feb. 2, 2022 (24 pages).

* cited by examiner

*Primary Examiner* — Kara D Johnson
*Assistant Examiner* — Maytee Marie Contes De Jesus
(74) *Attorney, Agent, or Firm* — Bookoff McAndrews, PLLC (57) ABSTRACT

The present disclosure provides fasciculated nerve grafts of customizable lengths and diameters, and methods of preparing the same. The grafts are made by digesting native extracellular matrix (ECM) around the nerve fascicles of a nerve tissue, and the epineurial sheath. One or more of the individual fascicles may then be entubulated in an entubulation material, embedded in or coated with a coating material, or both, to form a fasciculated nerve graft. The fasciculated nerve grafts are customizable and designed to bridge nerve gaps; the modularity of the fasciculated nerve graft allows for restoring continuity to nerve defects of virtually any length and allows for matching the diameter of the patient's recipient nerve.

22 Claims, 3 Drawing Sheets

FASCICULATED NERVE GRAFTS, METHODS OF MAKING THE SAME, AND METHODS OF TREATMENT USING THE SAME

CROSS-REFERENCE TO RELATED APPLICATIONS

This patent application claims the benefit of priority to U.S. Provisional Patent Application No. 63/104,437, filed on Oct. 22, 2020, the entirety of which is incorporated herein by reference.

TECHNICAL FIELD

The present disclosure relates generally to the fields of neurobiology and medicine. More particularly, the present disclosure relates to fasciculated nerve grafts, methods of making such nerve grafts, and methods of treating nerve deficits using such nerve grafts.

BACKGROUND

Nerve injury can cause various types of chronic pain, including neuropathic pain. Peripheral nerve injury is a common clinical challenge caused by a variety of accidental injuries and is on a sharp rise. Peripheral nerve injury often leads to paralysis, palsy, and loss of autonomous control over corresponding body area. While surgical repair of nerve injury is currently a common treatment for such injuries, the outcomes are less than ideal. As such, there is a need for new strategies to improve axonal regeneration and target organ innervation after nerve injury.

Neurons of the peripheral nervous system are understood to have higher intrinsic regeneration ability than the neurons of the central nervous system and can regenerate axons under suitable environmental conditions. However, the peripheral nerve regeneration process is complex and controlled by multiple factors, such as the microenvironment involved in nerve regeneration. Nonetheless, autologous nerve transplantation has been accepted as a gold standard for repairing peripheral nerve defects.

In many clinical situations, there is not enough nerve tissue to allow a tension-free reconstruction of peripheral nerve by direct end-to-end coaptation of the transected nerve. In these cases, nerve grafts of different sources can be used to bridge the nerve gap. Nerve autografts typically require a second operative site, which necessitates additional operative time, a permanent scar, and sensory loss in the region of the donor nerve, and could result in persistent postoperative pain. An alternative to a nerve autograft is the use of processed nerve allografts or processed nerve xenografts, both of which provide a biological substrate for nerve regeneration, and, like a nerve autograft, can be used without immunosuppression. Nonetheless, currently available commercial graft technologies are limited in that they may not be the right "fit match" for any particular surgical need. The quality, and availability of nerve grafts, particularly of the length and diameter size appropriate to any particular patient need, remains a challenge. Indeed, currently available commercial nerve grafts are of limited size, in terms of length and diameter, which may not fulfill all patients' needs.

SUMMARY

In accordance with the present disclosure, there is provided a fasciculated nerve graft comprising one or more nerve fascicles, wherein the fasciculated nerve graft is substantially free of epineurial sheath and of native extracellular matrix material.

In addition, in accordance with the present disclosure, there is provided a method of preparing a fasciculated nerve graft, the method comprising providing at least one nerve tissue comprising one or more nerve fascicles and comprising native extracellular matrix material and an epineurial sheath, treating the at least one nerve tissue with an enzyme that degrades the native extracellular matrix material and the epineurial sheath, washing the treated at least one nerve tissue to substantially remove and/or inactivate the enzyme and to substantially remove the native extracellular matrix material degradation products and the epineurial sheath degradation products, thereby producing the one or more nerve fascicles that are substantially free of the native extracellular matrix material and of the epineurial sheath; and forming a fasciculated nerve graft from at least one nerve fascicle of the one or more nerve fascicles that are substantially free of the native extracellular matrix material and of the epineurial sheath.

One of ordinary skill in the art will appreciate that the nerve grafts, methods of preparing nerve grafts, and methods of treatment using nerve grafts disclosed herein may be used in the surgical interventions of humans and other vertebrates, as well is in laboratory studies, comparisons, and assays.

One of ordinary skill in the art will also appreciate that starting materials, biological materials, biocompatible materials, components, growth factors, agents, enzymes, and solutions, therapies, drugs, and methods of preparation and treatment other than those specifically exemplified can be employed in the practice of the disclosure without resort to undue experimentation. All art-known functional equivalents of any such materials and methods are intended to be included in this disclosure.

The methodologies described herein to prepare and provide treatment using fasciculated nerve grafts may better enable use of low-yield donors, whose nerves might otherwise have been rejected for use based on their diameters or insufficient number of fascicles. For example, the present disclosure provides for combining fascicles isolated from more than one harvested nerve to create a fasciculated nerve graft of desired length and diameter. The disclosed methods thus may improve the yield of usable donor nerves, for example, and make the grafting process more efficient and economical.

Other objects, features and advantages of the present disclosure will become apparent from the following detailed description. It should be understood, however, that the detailed description and the examples, while indicating exemplary embodiments of the present disclosure, are given by way of illustration only, since various changes and modifications within the spirit and scope of the invention will become apparent to those skilled in the art from this detailed description. Note that simply because a particular compound is ascribed to one generic formula does not mean that it cannot also belong to another generic formula.

The singular forms "a," "an," and "the" include plural reference unless the context dictates otherwise. The terms "approximately" and "about" refer to being nearly the same as a referenced number or value. As used herein, the terms "approximately" and "about" generally should be understood to encompass ±5% of a specified amount or value. The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. Throughout this application, the term "about" is used to indicate that a value includes the inherent variation of error for the device, the method being employed to determine the value, or the variation that exists among the study subjects.

Both the foregoing general description and the following detailed description are exemplary and explanatory only and are not restrictive of the features, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." In addition, the term "between" used in describing ranges of values is intended to include the minimum and maximum values described herein.

The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of exemplary embodiments presented herein.

DETAILED DESCRIPTION

The nerve grafts of the present disclosure can be prepared in a wide variety of lengths and diameters to match a variety of operational needs. The present disclosure, therefore, may provide for more successful nerve regeneration and better patient outcomes. Exemplary nerve grafts, related methods for their preparation, and related methods of treatment using the nerve grafts are described in detail below.

According to some embodiments of the present disclosure, preparing a nerve graft includes providing a nerve tissue having one or more nerve fascicles.

Figure 1:
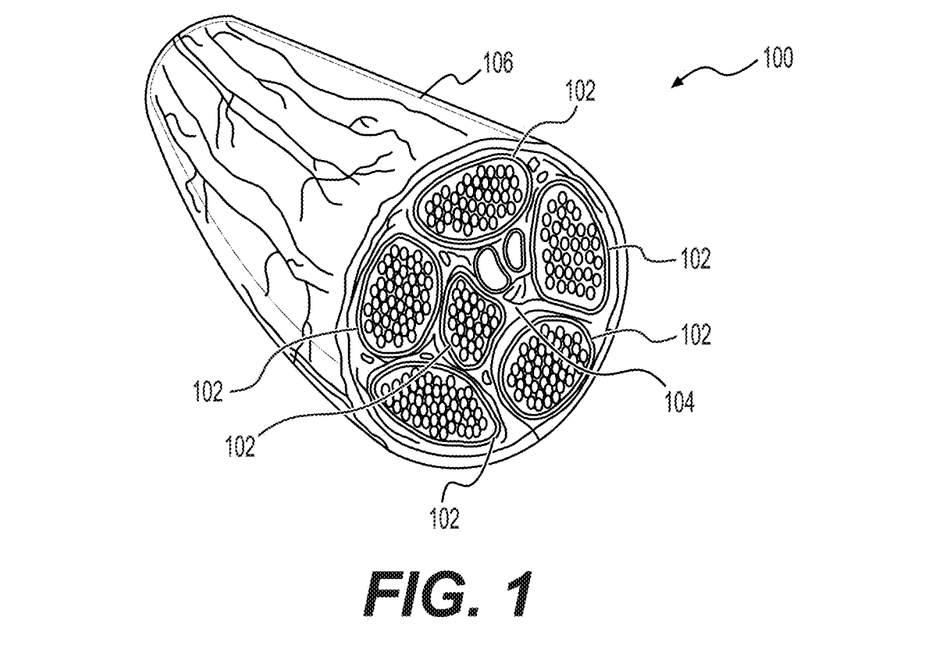
FIG. 1 shows a sectional view of peripheral nerve tissue.

FIGS. 1-4 illustrate an example of nerve tissue 100 used to prepare a fasciculated nerve graft 114. The particular features shown in FIGS. 1-4 are illustrative only and non-limiting of the scope of the present disclosure. FIG. 1 shows a sectional view of a nerve tissue 100, including nerve fascicles 102, native extracellular matrix (ECM) material 104, and an epineurial sheath 106. The nerve tissue 100 may include one nerve fascicle, or more than one nerve fascicle 102, as shown in FIG. 1. The nerve tissue 100 suitable for use in the present disclosure may be obtained from an animal, such as a mammal, e.g., a human or a non-human mammal. More than one nerve tissue 100 may be used in the methods described herein, and nerve fascicles 102 from more than one type of nerve tissue 100, for example, human nerve tissue and non-human nerve tissue, or non-human nerve tissue from different non-human mammals, may be combined in preparing a fasciculated nerve graft 114. A fasciculated nerve graft 114, shown in FIG. 4, may be prepared from nerve tissue 100 isolated from humans, non-human animals, or other vertebrates. The starting nerve material may be sourced from any suitable nerve tissue in the body. The starting nerve material may include peripheral nerve tissue or spinal nerve tissue, and may ultimately be used to form a nerve graft for peripheral or spinal nerve grafting.

Fasciculated nerve grafts (including illustrated fasciculated nerve graft 114) according to the present disclosure may be allogeneic or xenogeneic to a patient to be treated with the fasciculated nerve graft. In the example of FIGS. 1-4, the fasciculated nerve graft 114 comprises the three-dimensional microstructural scaffold of, and may comprise protein components inherent to, nerve tissue 100. Also contemplated herein are methods that include one or more immunosuppressive techniques performed on nerve tissue (such as nerve tissue 100) and/or fasciculated nerve grafts prepared from the nerve tissue (e.g., the fasciculated nerve graft 114 prepared from the nerve tissue 100) before and/or after implantation in a patient. For example, donated nerve tissue may be processed to selectively remove cellular components and/or debris prior to incorporating the fascicles in a fasciculated nerve graft and/or nerve tissue may be processed to selectively remove cellular components and/or debris prior to treatment according to the methods described herein.

Figure 4:
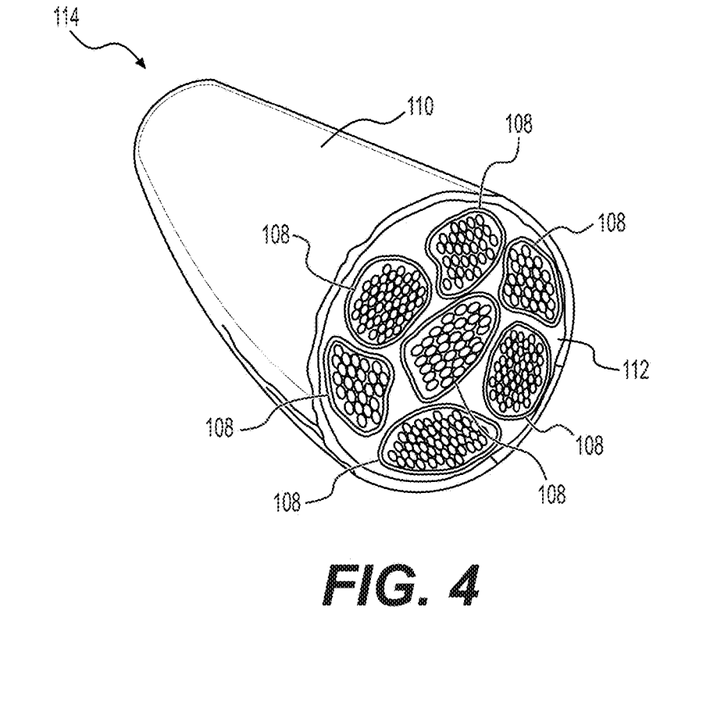
FIG. 4 shows a nerve graft formed from the nerve fascicles and the sheet of biomaterial shown in FIG. 3.

Preparation of the exemplary fasciculated nerve graft 114 according to the methods herein may include treating the nerve tissue 100 with one or more enzymes that at least partially or completely degrade the native ECM material 104 and the epineurial sheath 106. The enzyme(s) may include, for example, collagenase type IV, other types of collagenase (I or III, concentrations up to 1 mg/mL), or matrix metallopeptidases (MMPs) (for example, MMP7 or MMP12) in concentrations up to 1:20 within an aqueous-based solution, such as phosphate-buffered saline (PBS) or saline.

Treating nerve tissue (e.g., nerve tissue 100) with the enzyme(s) may be performed at a temperature between about 4° C. and about 37° C., such as between about 4° C. and about 15° C., between about 10° C. and about 20° C., or between about 20° C. and about 30° C. In addition, treating the nerve tissue 100 with the enzyme(s) may be performed for a period of time between about 2 hours to about 24 hours, such as between about 2 hours and about 5 hours, between about 8 hours and about 12 hours, between about 16 hours and about 24 hours, or between about 6 hours and about 12 hours. In at least one example, treating the nerve tissue 100 with the enzyme(s) may be performed for a period of time between about 2 hours to about 6 hours at a temperature of about 35° C. to about 40° C., and, more particularly, for a period of between about 2 hours to about 4 hours at a temperature of about 37° C. In at least one example, treating the nerve tissue 100 with the enzyme(s) may be performed for a period of time between about 4 hours to 24 hours at a temperature of about 4° C. to about 6° C. Treating the nerve tissue 100 with the enzyme(s) may be performed with agitation.

The treated nerve tissue, including individual nerve fascicles (e.g., nerve fascicles 102) can then be washed to remove any remaining enzymes and/or debris remaining from the treated nerve tissue. That is, the method may also include washing the treated nerve tissue to remove the enzyme(s), residual native ECM material, or epineurial sheath degradation products. In some aspects, washing the treated nerve tissue may inactivate the enzyme(s) by balancing the pH. The enzyme(s) may be completely or at least partially removed and/or inactivated by performing the washing step. Washing the treated nerve tissue may be performed using a solution, such as phosphate-buffered saline (PBS), a serine-containing serum, or a combination thereof, for example. Washing the treated nerve tissue may be performed with agitation. In addition, the step of washing the treated nerve tissue may be performed at a temperature between about 4° C. to about 40° C. Further, the step of washing the treated nerve tissue may be performed for a period of time between about 1 minute to about 4 hours. Still further, the step of washing the treated nerve tissue may be performed more than once, e.g., two, three, or four or more times. The treated nerve tissue may be sufficiently washed to remove the native ECM material and the epineurial sheath, thereby producing one or more nerve fascicles that do not include, or which are substantially free of the native ECM material and the epineurial sheath. As used herein, the phrase "substantially free of the native ECM material" means that all, or that at least 50% of the native ECM material is removed. In certain embodiments, one or more nerve fascicles that are substantially free of the native ECM material have had at least about 85% or at least about 95% of the native ECM material removed. In other embodiments, one or more nerve fascicles that are substantially free of the native ECM material have had at least about 99% or the entirety of the native ECM material removed. In addition, one or more of the nerve fascicles that are substantially free of the epineurial sheath have had at least about 95%, at least about 99%, or the entirety of the epineurial sheath removed.

Additionally or alternatively, the method may also include suspending and incubating the treated and washed nerve tissue in a solution. The incubation may be performed at a temperature between about 4° C. and about 37° C., such as between about 4° C. and about 15° C., between about 10° C. and about 20° C., or between about 20° C. and about 30° C. The incubation may be performed for a period of time of about 45 minutes to about 24 hours, such as between about 1 hour and about 2 hours, between about 3 hours and about 8 hours, between about 6 hours and about 12 hours, or between about 12 hours and about 24 hours. For example, the incubation may be for a period of time of 6 hours to about 24 hours at a temperature of about 4° C. In another example, the incubation may be for a period of time of about 45 minutes to 60 minutes at a temperature of about 37° C. In some aspects, the incubation may be for a period of time of about 3 hours to about 5 hours at 37° C., for example for about 4 hours at 37° C. While exemplary ranges of durations and temperatures are listed herein, in general, as the incubation temperature decreases, the duration of the incubation may increase. The suspending the nerve tissue, incubating the nerve tissue, or both may also be performed with agitation. The solution used for suspension and incubation may include serine components, including at least alpha-antitrypsin and alpha-2-macroglobulin. The solution may be a serine-containing serum. For example, the solution may comprise fetal bovine serum, goat serum, horse serum, porcine serum, sheep serum, chicken serum, or rabbit serum.

Additionally or alternatively, the method may also include a step of washing the suspended and incubated nerve tissue with a buffered solution to remove the solution used in the step of suspending the washed nerve tissue. The buffered solution may have a pH between about 6.8 and about 7.8, such as, e.g., about 7.2, about 7.4, or about 7.6. In at least one example, the suspended nerve tissue may be washed with the buffered solution for a period of time of about 45 minutes to about 55 minutes at a temperature of about 37° C. In at least one example, the suspended nerve tissue may be washed with the buffered solution for a period of time of about 1 hour to about 6 hours at a temperature of about 4° C. In addition, the step of washing the suspended nerve tissue with the buffered solution may be performed with agitation. The buffered solution may comprise, for example, phosphate buffered saline or other suitable buffers.

Figure 2:
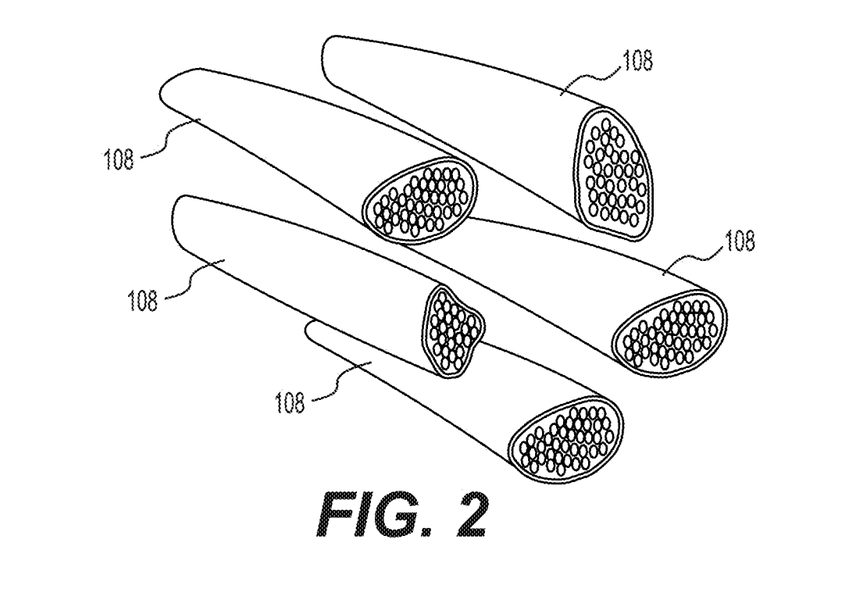
FIG. 2 shows nerve fascicles of the peripheral nerve tissue shown in FIG. 1, following removal of an epineurial sheath and native extracellular matrix material, and the separation of the individual nerve fascicles.
Figure 3:
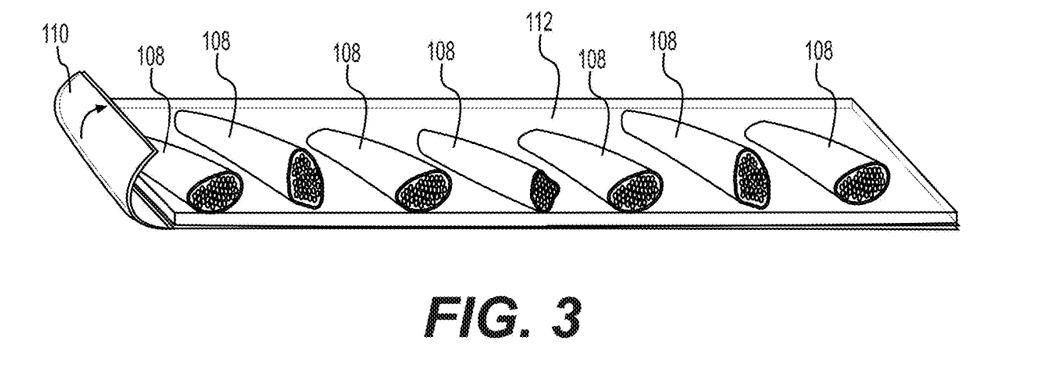
FIG. 3 shows individual nerve fascicles as those shown in FIG. 2, placed on a sheet of biomaterial.

The nerve fascicles of the treated and washed nerve tissue may then be separated from each other, thereby producing separated nerve fascicles. FIG. 2 shows five separated nerve fascicles 108 derived from nerve tissue 100 (that is, the five separated nerve fascicles 108 of FIG. 2 corresponding to five of the six nerve fascicles 102 depicted in FIG. 1). Any number of separated nerve fascicles can then be substantially aligned (optionally in combination with one or more nerve fascicles obtained from one or more other samples of nerve tissue—including wherein those samples of nerve tissue are obtained from different sources), and the non-end sides entubulated by wrapping or rolling to prepare the fasciculated nerve graft (e.g., fasciculated nerve graft 114) containing one or more nerve fascicles, without or substantially free of the native ECM material and/or the epineurial sheath. FIG. 3 shows seven separated nerve fascicles 108, including the five separated nerve fascicles 108 derived from nerve tissue 100 shown in FIG. 3, and two additional separated nerve fascicles 108 derived from a different nerve tissue. That is, with reference to FIGS. 3 and 4, the fasciculated nerve graft 114 may be formed from at least one separated nerve fascicle (e.g., a plurality of separated nerve fascicles 108) and an entubulation material 110 comprising a biocompatible material that surrounds the nerve fascicle(s) 108. All nerve fascicles 108 used to form the fasciculated nerve graft 114 may be from the same nerve tissue, or one or more of the nerve fascicles 108 may be combined with one or more other fascicles, which have been obtained from other nerve tissue. Such other nerve fascicle(s) may be obtained from nerve tissue treated and washed in the same manner as described above.

Figure 5:
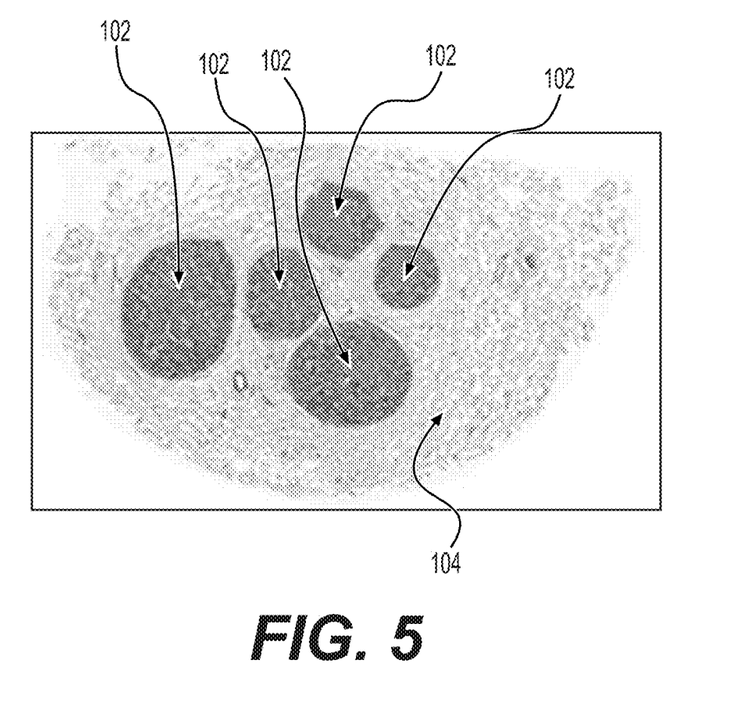
FIG. 5 shows stained nerve tissue reflecting nerve fascicles and extracellular matrix material, prior to treatment of the nerve tissue with an enzyme.
Figure 6:
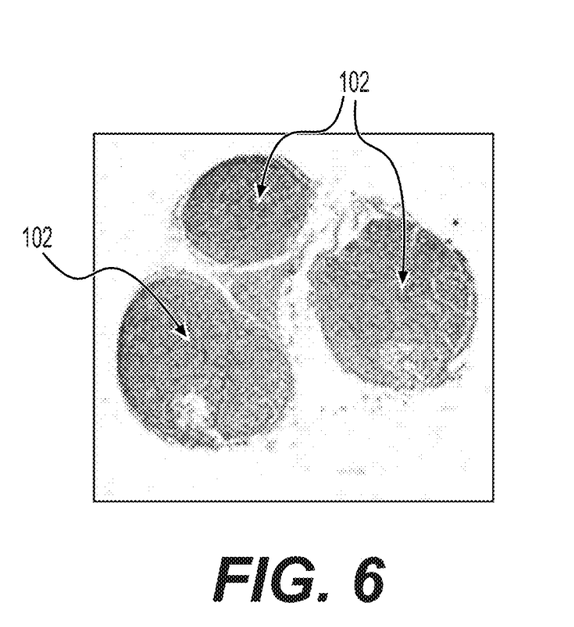
FIG. 6 shows stained nerve fascicles after the nerve tissue was treated with enzyme.

The individual fascicles used to prepare a fasciculated nerve graft according to the present disclosure (e.g., fasciculated nerve graft 114) are substantially unaltered and undamaged by the processing methods used in treating the nerve tissue (e.g., nerve tissue 100), as well as subsequent washes and incubations. The enzyme(s) substantially digest the native ECM material of the nerve tissue (e.g., the native ECM material 104 of the nerve tissue 100) and the epineurial sheath (e.g., the epineurial sheath 106), without substantially damaging the nerve fascicles. Enzymes appropriate for digesting the native ECM material and the epineurial sheath without altering or damaging the nerve fascicles include those mentioned above, e.g., specific and non-specific collagenases or collagen-specific enzymes or chemicals. For example, collagenase type IV may be used to remove the native ECM material and the epineurial sheath. The enzymes that do not alter or damage the nerve fascicles are those that leave the fascicles and a perineurium surrounding each fascicle substantially intact and of sufficient quality for handling of the nerve fascicles. In addition, the perineurium surrounding each fascicle may be impacted during the processing of the nerve tissue, while remaining substantially intact and of sufficient quality for handling the nerve fascicles. As used herein, the term "substantially intact and of sufficient quality for handling" means one or more of the following: the nerve fascicle has the ability to be manipulated, e.g., picked up using a tool, such as forceps, without the nerve fascicle falling apart, the nerve fascicle may maintain the form and shape similar to a nerve fascicle in the native nerve tissue (e.g., a nerve fascicle 102 in the nerve tissue 100), the nerve fascicle remains in a solid state with no flowability, or the physical characteristics of the nerve fascicles, such as tensile strength and elastic modulus, for example, may be similar to those of nerve fascicles in the native nerve tissue (e.g., the nerve fascicles 102 of the nerve tissue 100). FIG. 5 shows laminin-stained nerve fascicles 102 surrounded by the native ECM material 104, prior to treatment with one or more enzymes according to the methods herein. FIG. 6 shows the same laminin-stained nerve fascicles 102 after treatment, wherein the nerve fascicles 102 remained intact while the native ECM material 104 and the epineurial sheath 106 is removed. Example 1 below describes a method of treating and washing nerve tissue, such as nerve tissue 100, according to the present disclosure.

According to some embodiments, the processed, separated nerve fascicles are aligned (if more than one fascicle is used) and entubulated, including by being wrapped with an entubulation material, which is a biocompatible material. The entubulation material may be any material of sufficient strength that has the ability to be manipulated, e.g., picked up with a tool, such as forceps, while maintaining its shape, and may be, for example, a sheet, a sheath, a tube, a gel, or an adhesive. The entubulation material may be any material that is able to hold the fascicles together in a shape that is representative of a shape of a native nerve (e.g., the nerve tissue 100). In addition, the entubulation material may be formed of any material or combinations of materials of sufficient strength that has the ability to withstand insertion of sutures therethrough for attachment of the entubulation material to a nerve end or another material. FIG. 3 illustrates an exemplary entubulation material 110 in the form of a sheet as shown in FIG. 3. Alternatively, the nerve fascicles (e.g., nerve fascicles 108) may be entubulated by surrounding the non-end sides of the fascicles with a tube comprising biocompatible material. The entubulation material may comprise various materials or combinations of materials, which may be natural or synthetic. Exemplary biocompatible materials suitable for use as the entubulation material that forms the fasciculated nerve grafts herein include, but are not limited to, intact ECM, collagen (including, but not limited to, isolated type-I collagen, or additional types of collagen, including types II, III, IV, V, and VI), synthetic biodegradable materials (such as polyester, like polylactide (PLA), polylactiv-co-glycolic acid (PLGA), poly-L-lactic acid (PLLA), polyethylene glycol (PEG), or polycaprolactone (PCL)), polysaccharides (including, e.g., chitosan, alginate, cellulose), polydioxanone (PDS), polymers (including, e.g., protein-based polymers), fibrinogen, fibrin, gelatin, and hydrogels. The biocompatible material used as the entubulation material may be biodegradable. Further details of suitable biocompatible materials are listed below. The sheet of the entubulation material may be positioned to encircle and to contain one or more individual nerve fascicles in configurations and dimensions as desired, including configurations and dimensions customized to a patient's needs. In some examples, a biocompatible adhesive or sealant may be used to prepare the fasciculated nerve graft. For example, to the extent the entubulation material comprises one or more seams in need of closure (e.g., a sheet rolled into a tube), the seam(s) may be closed (e.g., edges of the sheet may be joined and sealed together) through use of a biocompatible adhesive or sealant. Examples of adhesives or sealants that may be used to close the seam according to the present disclosure include, but are not limited to, biologically-sourced or synthetic materials, including but not limited to PEG, fibrin glue, isolated type-I collagen (or additional types of collagen, including types II, III, IV, V, and VI), and photo curing adhesives. The sealant or adhesive may ensure similar mechanical properties and elastic modules as the peripheral nerve tissue.

Alternatively or in addition to the step of entubulating the at least one nerve fascicle (e.g., nerve fascicle 108), preparing the fasciculated nerve graft (e.g., fasciculated nerve graft 114) may include a step of embedding or coating the nerve fascicles in or with a coating material that is a biocompatible material or combination of biocompatible materials. The coating material may be in gel form, for example, or may comprise an adhesive, or both a gel and an adhesive. The biocompatible material used as the coating material may be the same as or different than the biocompatible materials described above for use as the entubulation material, in a case in which the nerve fascicles are wrapped in the entubulation material and embedded or coated with the coating material. For example, after aligning the nerve fascicles on the entubulation material, the aligned nerve fascicles may be embedded in the coating material and then wrapped in the entubulation material. Alternatively, for example, the nerve fascicles may be embedded or coated with the coating material, before being aligned on the entubulation material and wrapped in the entubulation material. And, as another alternative to the coating step, the entubulation material may be slathered with the coating material (that is, the coating material (e.g., coating material 112, shown in FIGS. 3 and 4) is spread on the entubulation material), before aligning the nerve fascicles on the entubulation material and wrapping the nerve fascicles in the entubulation material.

Further, alternatively or in addition to the step of embedding or coating the nerve fascicles, preparing the fasciculated nerve graft may include a step of at least partially or completely filling a space between the nerve fascicles with a filling material, comprising a biocompatible material or a combination of biocompatible materials, including one or more of a gel, collagen, gelatin, a polysaccharide, a hydrogel, fibrin, fibrinogen, alginate, cellulose, chitosan, or extracellular matrix material. The biocompatible material used as the filling material may be the same or different than the biocompatible material used as the entubulation material, and may be the same or different than the biocompatible material used as the coating material, in a case in which the filling step is performed in addition to the step of coating the nerve fascicles. For example, a layer of the filling material may fill space between the nerve fascicle(s) and the entubulation material, and/or spaces between nerve fascicles. That is, the method of preparing the fasciculated nerve graft may include, for example, after aligning the nerve fascicles on the entubulation material and wrapping the aligned nerve fascicles in the entubulation material, the filling material may be added, for example, by injection, to a space within the entubulation material between the entubulated nerve fascicles.

The methods herein can be used to produce nerve grafts of desired dimensions, having a desired length, perimeter, and cross-sectional dimension (width, such as diameter in the case of a cylindrical nerve graft). To that end, the number of individual nerve fascicles used to prepare a fasciculated nerve graft may comprise any number of nerve fascicles appropriate for achieving a nerve graft of a desired width (or diameter), and for example, may contain two or more fascicles. That is, in some embodiments, the fasciculated nerve graft includes a single nerve fascicle, and, in other embodiments, the fasciculated nerve graft includes more than one nerve fascicle 108. For example, the fasciculated nerve graft may comprise a plurality of fascicles, such as at least 2, at least 3, at least 4, at least 5, at least 8, at least 10, at least 12, or at least 16 nerve fascicles. In some examples, the nerve graft comprises 2 to 20 nerve fascicles, 5 to 15 nerve fascicles, 14 to 18 nerve fascicles, or even more than 20 nerve fascicles, depending on the size of the nerve fascicles, the location in the patient's body in which the fasciculated nerve graft is to be used, and properties of the nerve to which the fasciculated nerve graft will be attached.

The fasciculated nerve graft (e.g., fasciculated nerve graft 114) may have dimensions suitable for the surgical needs of a patient, and the number of nerve fascicles used to form the fasciculated nerve graft may be determined, at least in part, based on dimensions of the one or more nerve fascicles and the desired dimensions of the fasciculated nerve graft, including as determined by its location of use and the particulars of the surgical site within a patient. According to some aspects of the present disclosure, the fasciculated nerve graft may include nerve fascicles that are substantially similar to one another in diameter, alternatively the fasciculated nerve graft may comprise two or more individual nerve fascicles of substantially dissimilar diameter from one another, and further, the fasciculated nerve graft may comprise individual nerve fascicles, some of which have substantially similar diameters as one another, and others of which have substantially dissimilar diameters to one another. The diameter of each nerve fascicle (e.g., each nerve fascicle 108) may be between about 50 μm and about 1 mm, between about 50 μm and about 5 mm, e.g., between about 100 μm and about 500 μm, between about 250 μm and about 750 μm, between about 600 μm and about 900 μm, between about 750 μm and about 1 mm, or between about 750 μm and about 5 mm.

The size of the fasciculated nerve graft is selected to match a fascicular area and/or a total diameter of a recipient nerve. Thus, the number and size of the fascicles used to form the nerve graft may be selected to match an overall size of the fasciculated nerve graft to the number and/or size of fascicles of the recipient nerve. The fasciculated nerve graft (e.g., fasciculated nerve graft 114) may have a diameter between about 50 μm and about 10 mm, e.g., between about 100 μm and about 500 μm, between about 250 μm and about 750 μm, between about 600 μm and about 900 μm, or between about 750 μm and about 5 mm. An individual fascicle may have a minimum diameter of about 10 μm. For any single desired diameter of the fasciculated nerve graft, it may be possible to prepare the fasciculated nerve graft from one fascicle or more than one fascicle. In a case in which the fasciculated nerve graft is formed of more than one nerve fascicle, the nerve fascicles used to form the fasciculated nerve graft may be substantially similar in diameter. As used herein, "substantially similar in diameter" means that the nerve fascicles have diameters within ±20% of each other. Alternatively, the nerve fascicles used to form the fasciculated nerve graft may be different from each other. And, as noted above, the number of fascicles used may depend on the size of the nerve fascicles, as well as the location in the patient's body in which the fasciculated nerve graft is to be used, and properties of the nerve to which the fasciculated nerve graft will be attached.

The methods of forming fasciculated nerve grafts (e.g., fasciculated nerve graft 114) herein may include a step of modifying the lengths of a plurality of nerve fascicles (e.g., nerve fascicles 108), to provide, e.g., a plurality of nerve fascicles of substantially the same length as one another. For example, the nerve fascicles may be, e.g., trimmed or cut by any appropriate technique, before during, or after combining the nerve fascicles into the fasciculated nerve graft prepared by any of the methods described above, which may include one or more of the steps of entubulating, embedding or coating, and/or filling, as described above. In some aspects, each nerve fascicle should continue from one end to the other end of the nerve graft to best prevent axonal escape or formation of a neuroma. The fasciculated nerve graft may be formed so as to have a length between about 3 mm and about 200 mm, such as between about 5 mm and about 100 mm, between about 20 mm about 50 mm, between about 45 mm and about 75 mm, or between about 15 mm to about 40 mm in length. Further, for example, the fasciculated nerve graft may define a total volume ranging from about 5 $mm^3$ to about 55,000 $mm^3$, such as about 100 $mm^3$ to about 25,000 $mm^3$, about 500 $mm^3$ to about 10,000 $mm^3$, about 1,000 $mm^3$ to about 5,000 $mm^3$, about 500 $mm^3$ to about 2,000 $mm^3$, about 100 $mm^3$ to about 5000 $mm^3$, or about 7,500 $mm^3$ to about 15,000 $mm^3$.

The fasciculated nerve grafts (e.g., fasciculated nerve graft 114) described herein may also include one or more of a nerve growth factor, a cell, a mix of cells, including multiple cell types in a mixed cell population, a cellular component, a non-steroidal anti-inflammatory agent, or an immunosuppressive agent, any of which may be included at any time in the formation of the fasciculated nerve graft, and/or may be added to the fasciculated nerve graft after its formation. In addition, immunosuppressive techniques and immunophilic agents described in U.S. Provisional Application No. 63/071,635, which is incorporated by reference herein in its entirety, may be used for regenerative activity and immunosuppressive activity in the fasciculated nerve graft of the present disclosure.

The fasciculated nerve grafts (e.g., fasciculated nerve graft 114) prepared according to the methods described herein may be used in a method of treating a patient to, for example, reconstruct peripheral nerve discontinuities in order to support axonal regeneration across a nerve gap. The patient may be a human or a non-human animal (e.g., cat, dog, horse, etc.). For example, a fasciculated nerve graft used in treatment according to the methods herein may be transplanted through a surgical procedure. In an exemplary procedure, the surgeon or other medical professional may examine the patient's tissue at the site of interest and resect scar tissue, if needed. Proximal and distal segments of the injured nerves may be debrided to healthy tissue, e.g., by visual and tactile signs. Further, the surgeon may measure the distance between ends of nerves defining the nerve gap and the diameter of the damaged nerve, in order to select a fasciculated nerve graft of the appropriate length and diameter. The fasciculated nerve graft, prepared according to the present disclosure, may then be implanted into the patient. The surgeon may use sutures to connect the fasciculated nerve graft to the ends of the nerves defining the nerve gap. Optionally, treating the patient may also include analgesic therapy and/or administration of a non-steroidal anti-inflammatory drug, a growth factor, or an immunosuppressive agent. Such agents may be introduced into the fasciculated nerve graft, as mentioned above, and/or may be administered to the patient separately. Non-steroidal anti-inflammatory agents, such as nonsteroidal anti-inflammatory drugs (NSAIDs), like ibuprofen, may reduce pain, decrease fever, prevent blood clots, and in relatively higher doses, decrease inflammation. Such NSAIDs may be non-selective, to inhibit the activity of both cyclooxygenase enzymes (COX-1 and COX 2), or COX-2 selective, used to inhibit the activity of COX-2. Immunosuppressive agents may help prevent unwanted immune responses against an implanted fasciculated nerve graft. Immunosuppressive agents useful for the present disclosure may include, but are not limited to, steroids (including, but not limited to, testosterone and estrogen), glucocorticoids, cytostatics, antibodies, drugs acting on immunophilins, and other immunosuppresive drugs. Immunophilin ligands, such as FK506, provide the immunosuppressive properties, whilst improving nerve regeneration through an independent mechanism of action.

As described above, the fasciculated nerve grafts (e.g., fasciculated nerve graft 114) described herein may be formed by combining one or more nerve fascicles (e.g., nerve fascicles 108) with one or more biocompatible materials, as well as other optional supplemental materials. In particular, the nerve fascicles may be entubulated (e.g., wrapped in, or surrounded by) in an entubulation material (e.g., entubulation material 110 shown in FIGS. 3 and 4), embedded in or coated with a coating material (e.g., coating material 112 shown in FIGS. 3 and 4), and/or surrounded by a filling material, wherein the entubulation material, the coating material, and/or the filling material comprise one or more biocompatible materials, including biocompatible material(s) that are biodegradable, to form the fasciculated nerve grafts. The biocompatible materials listed below may be used to fill the spaces between the fascicles. The biocompatible materials may be used to embed the fascicles within the final construct (that is, the final fasciculated nerve graft). In some aspects, the biocompatible materials may be used to coat the outer layer of the final product. As described in more detail below, various materials, including one or more of non-native ECM material, collagen, chitosan, alginate, a biodegradable polymer, cellulose, fibrinogen, fibrin, a protein-based polymer, gelatin, polysaccharides (other than chitosan, alginate, or cellulose), optionally in the form of a hydrogel, may be used for the purpose of entubulating and/or embedding or coating one or more nerve fascicles, and/or filling a space around the one or more nerve fascicles. The ECM materials and the proteins listed are considered as general biocompatible proteins that will allow stabilization of the nerve fascicles within the fasciculated nerve grafts and help prevent soft tissue infiltration within the implanted tissue.

As noted above, the entubulating material and/or the coating material may include non-native ECM material, that is, ECM material that is added after some portion of the native ECM material and the epineurial sheath are removed. Non-native ECM materials may be sourced from different types of tissue or from different species. In addition, non-native ECM materials comprise proteins that may include, but are not limited to, laminin (e.g., laminin alpha-2, laminin alpha-4, laminin alpha-5, laminin beta-1, laminin beta-2, laminin gamma-1), collagen (e.g., collagen IV alpha-1(IV) chain, collagen IV alpha-1/5(IV) chain, collagen alpha IV-2 chain, collagen alpha IV-3 chain, collagen I alpha-1 chain, collagen alpha-2(I) chain, collagen alpha-3(VI) chain, collagen alpha-1(VI) chain, collagen alpha-1(XXVIII) chain, collagen alpha-1(III) chain, collagen alpha-3(V) chain, collagen alpha-1(XVI) chain, collagen alpha-1(XXI) chain, collagen alpha-2(VI) chain, collagen alpha-1(VIII) chain, collagen alpha-1(V) chain, collagen alpha-1(II) chain, collagen alpha-1(XIV) chain, collagen alpha-1(XII) chain), fibronectin (e.g., fibronectin 1 (type-III 4,7 domain)), asporin, perlecan, nidogen (e.g., nidogen-1, nidogen-2), lumican, dermatopontin, keratin, type II cytoskeletal 1, fibrillin-1, decorin, vitronectin, myelin protein P0, myelin P2 protein, asporin, prolargin, biglycan, periostin, and alpha-crystallin B chain. Of these, at least the following proteins are believed to contribute to the regenerative capacity of the nerve graft: laminin alpha-2, laminin alpha-4, laminin alpha-5, laminin beta-1, laminin beta-2, laminin gamma-1, collagen iv alpha-1(IV) chain, collagen IV alpha-1/5(IV) chain, collagen alpha IV-2 chain, collagen alpha IV-3 chain, fibronectin 1 (type-iii 4, 7 domain), perlecan, nidogen-1, and nidogen-2. The non-native ECM material(s) may comprise one or more of the types of native ECM material that existed in the nerve tissue, prior to its processing and from which the one or more nerve fascicles are obtained.

The biocompatible material that is the entubulation material and/or the coating material may additionally or alternatively include one or more types of collagen. The collagen may be in the form of scaffolds formed of thin sheets, for example. Collagen I is particularly contemplated although other types of collagen, such as collagen II, III, IV and/or V may be included in the composition as well. Other types of collagen, grouped as fibrillar (Type I, II, III, V, XI), non-fibrillar, FACIT (Fibril Associated Collagens with Interrupted Triple Helices) (Type IX, XII, XIV, XIX, XXI), short chain (Type VIII, X), basement membrane (Type IV), multiplexin (Multiple Triple Helix domains with Interruptions) (Type XV, XVIII), MACIT (Membrane Associated Collagens with Interrupted Triple Helices) (Type XIII, XVII), or other (Type VI, VII) collagens, may be included. In general, collagen I and collagen III may be preferred, as these types of collagen comprise the native ECM material. These collagens may be derived from bovine, equine, porcine, or human sources, for example, and may be used in combination with silicones, glycosaminoglycans, fibroblasts, and/or growth factors.

The fasciculated nerve graft (e.g., fasciculated nerve graft 114) may additionally or alternatively include one or more polysaccharides, as a biocompatible material. Any type of biocompatible, biodegradable polysaccharide may be used. Such polysaccharides may include, but are not limited to, chitosan, alginate, or cellulose. Cellulose may include any one or more type of cellulose I, II, III or IV.

The fasciculated nerve graft (e.g., fasciculated nerve graft 114) may include one or more biocompatible polymers, such as one or more biodegradable polymers. Additionally or alternatively, the fasciculated nerve graft (e.g., fasciculated nerve graft 114) may include one or more protein-based polymers. In some examples, the fasciculated nerve graft (e.g., fasciculated nerve graft 114) may comprise polyethylene glycol (PEG), also known as polyethylene oxide (PEO) or polyoxyethylene (POE), depending on its molecular weight.

The fasciculated nerve graft (e.g., fasciculated nerve graft 114) may additionally or alternatively include fibrin (also called Factor Ia) and/or fibrinogen. Fibrin or fibrinogen may promote stabilization of the fascicles and the fasciculated nerve graft in general.

The fasciculated nerve graft (e.g., fasciculated nerve graft 114) may additionally or alternatively include gelatin, which is derived from collagen. Gelatin may also be referred to as hydrolyzed collagen, collagen hydrolysate, gelatine hydrolysate, and/or hydrolyzed gelatine. Gelatin may promote stabilization of the fascicles and the fasciculated nerve graft in general.

The fasciculated nerve graft (e.g., fasciculated nerve graft 114) may include hydrogels. The hydrogel may consist of, and is not limited to, any one or a combination of cellulose, any derivatives of cellulose, or hyaluronic acid. The hydrogel may be cross-linked to adjust the mechanical properties of it as well. The hydrogel may have a natural source or a synthetic source.

The fasciculated nerve graft (e.g., fasciculated nerve graft 114) additionally or alternatively may include nerve growth factor (NGF), which may be expressed as a 7S, 130-kDa complex of 3 proteins—α-NGF, β-NGF, and γ-NGF (2:1:2 ratio) (proNGF (NGF precursor)), or may be one of the following types: brain-derived neurotrophic factor (BDNF), neurotrophin-3 (NT-3), neurotrophin-4 (NT-4, and also known as NT4, NT5, NTF4, and NT-4/5), the endogenous steroids dehydroepiandrosterone (DHEA), and/or the sulfate ester thereof, namely DHEA sulfate (DHEA-S). Nerve growth factors may increase the number of neurons that regenerate their axons, which can enhance motor and sensory recovery and target muscle innervation.

Steroids, such as testosterone and/or estrogen, may also be used in the fasciculated nerve graft 114.

The fasciculated nerve graft (e.g., fasciculated nerve graft 114) may additionally or alternatively include a cell, a mix of cells, including multiple cell types in a mixed cell population, and/or a cellular component. Cell types for the cell and the mix of cells in the mixed cell population include, but are not limited to, Schwann cells, macrophages, adipocytes, exosomes from the Schwann cells, and the mentioned cells types. The source of the cells can be human derived or differentiated from stem cells or transdifferentiated from induced pluripotent stem cells. The added cells may be a source of cytokine and other factors, which may improve nerve regeneration.

As described above, the fasciculated nerve graft (e.g., fasciculated nerve graft 114) may be disposed in, stored in, and/or prepared in and/or with a buffer solution. With respect to storage, the fasciculated nerve graft may be placed in a storage container that is then maintained at a temperature ranging from about −80° C. to room temperature (about 20° C. to about 22° C.). The storage container may be amenable to flash freezing and maintenance at −80° C., or lower, for weeks, months, or years. The storage container may also be substantially air-tight and backfilled with inert gas. In some examples, the tissue is treated as disclosed herein (e.g., with an enzyme, or a digestion solution, and one or more washes with a serine-containing serum that may include a buffer solution, and optionally with additional washes comprising buffer solution) and then transferred to a buffer solution, e.g., a buffered saline solution, having a pH in the range of about 7.2 to about 7.6, e.g., a pH of about 7.3 to about 7.5, such as a pH of about 7.4, for storage prior to use in a medical procedure. Exemplary buffer solutions suitable for storing the grafts prepared according to the methods herein include, but are not limited to, PBS, saline catholytes, Tris-buffered saline, cacodylate buffer, Sorensen's phosphate buffer, phosphate-citrate buffer, and barbital buffer.

EXAMPLES

The disclosure may be further understood by the following non-limiting examples. The examples are intended to illustrate embodiments of the above disclosure, and should not be construed as to narrow its scope. One skilled in the art will readily recognize that the examples suggest many other ways in which the embodiments of the disclosure could be practiced. It should be understood that numerous variations and modifications may be made while remaining within the scope of the disclosure.

Example 1

Nerve tissue is treated to remove native ECM material and the epineurial sheath prior to preparation of a fasciculated nerve graft as follows. The following steps were performed under aseptic conditions, in a laminar flow hood. First, 100 µl of a collagen type IV specific digestive enzyme (for example, 0.8 mg/mL Collagenase IV) solution was transferred into 1.5 ml centrifuge tubes. Nerve tissue segments (about 3 mm long) and 100 µl (pipette setting) of the corresponding enzyme solutions were placed in the 1.5 ml centrifuge tubes, for incubation for 2 hours to 4 hours at 37° C. The digestive enzyme solution was aspirated using a bulb type transfer pipette, using extreme care so as to not physically damage the segments. The segments were then washed three times with 1 ml of PBS, mixing gently by inversion between washes. The washes were removed with a transfer pipette as above. As much fluid as possible was removed between each wash, ensuring not to damage segment. Touching between the test segments and the bulb transfer pipette tip was avoided.

Next, the aspirated PBS was replaced with, for example, 500 µl of fetal bovine serum (FBS), followed by incubation at 37° C. for 45 minutes to 55 minutes. Media was then aspirated from the 1.5 ml centrifuge tubes, ensuring not to damage the segments. These steps, that is, replacing aspirated media with FBS, incubating 45 minutes to 55 minutes at 37° C., and removing from the incubator and aspirate media, were repeated twice. Media was aspirated from the 1.5 ml centrifuge tubes, and replaced with 1 ml of PBS. Then, using a dissecting scope, a pair fine surgical forceps (e.g., number 5 jeweler forceps) was used to tease the visually separated fascicles from the rest of the digested tissue of each segment. A pair of microscissors was used to carefully debride the fascicles from the digested tissue.

Example 2

Nerve tissue obtained from an animal or a human source was prepared according to the procedure of Example 1 using collagenase type IV enzyme to digest, e.g., the native ECM material and the epineurial sheath of the nerve tissue. Nerve tissue not subjected to such processing was used as a control. The control nerve tissue and the treated nerve tissue were each embedded in paraffin. Cross sections of the nerve samples with thickness of 8 microns were obtained. The sections were then stained for laminin to identify the nerve fascicles. A histological bluing reagent was used to identify the presence of native ECM material. As shown in FIG. 5, the control nerve tissue included native ECM material around the nerve fascicles, whereas as shown in FIG. 6, the treated nerve tissue had little to no native ECM material around the nerve fascicles.

It should be understood that although the present disclosure has been made with reference to preferred embodiments, exemplary embodiments, and optional features, modifications and variations of the concepts herein disclosed may be resorted to by those skilled in the art, and that such modifications and variations are considered to be within the scope of this disclosure as defined by the appended claims. The specific embodiments and examples provided herein are examples of useful embodiments of the present disclosure and are non-limiting and illustrative only. It will be apparent to one skilled in the art that the present disclosure may be carried out using a large number of variations of the devices, device components, methods, and steps set forth in the present description. As will be recognized by one of skill in the art, methods and devices useful for the present methods can include a large number of various optional compositions and processing elements and steps.

What is claimed is:

1. A fasciculated nerve graft comprising:
    one or more nerve fascicles; and
    an entubulation material comprising a biocompatible material, the entubulation material entubulating the one or more nerve fascicles,
    wherein the fasciculated nerve graft is substantially free of epineurial sheath and of native extracellular matrix material.

2. The fasciculated nerve graft of claim 1, comprising a single nerve fascicle.

3. The fasciculated nerve graft of claim 1, comprising two or more nerve fascicles.

4. The fasciculated nerve graft of claim 3, comprising 2 nerve fascicles to 20 nerve fascicles.

5. The fasciculated nerve graft of claim 3, wherein the fasciculated nerve graft comprises nerve fascicles that are substantially similar to one another in diameter.

6. The fasciculated nerve graft of claim 5, wherein a diameter of each of the nerve fascicles is between about 50 µm and about 1 mm.

7. The fasciculated nerve of graft of claim 1, wherein the fasciculated nerve graft has a diameter of between about 50 µm and about 1 mm.

8. The fasciculated nerve graft of claim 3, wherein the fasciculated nerve graft comprises nerve fascicles that are substantially similar to one another in length.

9. The fasciculated nerve graft of claim 1, wherein the fasciculated nerve graft has a length of between about 3 mm and about 200 mm.

10. The fasciculated nerve graft of claim 1, wherein the one or more nerve fascicles are embedded in or coated with a coating material comprising a biocompatible material.

11. The fasciculated nerve graft of claim 10, wherein the biocompatible material of one or both of the entubulation material or the coating material is biodegradable.

12. The fasciculated nerve graft of claim 10, wherein the biocompatible material of one or both of the entubulation material and the coating material is an extracellular matrix material comprising one or more of a collagen, a chitosan, an alginate, a biodegradable polymer, a cellulose, a fibrinogen, a fibrin, a protein-based polymer, a gelatin, a polysaccharide, a hydrogel, or a non-native extracellular matrix material.

13. The fasciculated nerve graft of claim 1, wherein a gel, a collagen, a gelatin, a polysaccharide, a hydrogel, a fibrin, a fibrinogen, an alginate, or a non-native extracellular matrix material is also surrounded by the entubulation material.

14. The fasciculated nerve graft of claim 1, wherein the entubulation material comprises a seam and the seam is sealed by a biocompatible adhesive or sealant.

15. The fasciculated nerve graft of claim 1, wherein the one or more nerve fascicles are from a human, a non-human animal, or both.

16. The fasciculated nerve graft of claim 1, wherein the fasciculated nerve graft further comprises one or more of a growth factor, a cell, a mix of cells including multiple cell types in a mixed cell population, a cellular component, a non-steroidal anti-inflammatory agent, or an immunosuppressive agent.

17. The fasciculated nerve graft of claim 1, wherein the fasciculated nerve graft is a peripheral nerve graft or a spinal nerve graft.

18. The fasciculated nerve graft of claim 1, wherein at least about 50%, at least about 85%, at least about 95%, at least about 99%, or the entirety of the native extracellular matrix material has been removed.

19. The fasciculated nerve graft of claim 1, wherein at least about 95%, at least about 99%, or the entirety of the epineurial sheath has been removed.

20. The fasciculated nerve graft of claim 1, wherein about 50%, about 85%, about 95%, about 99%, or the entirety of the native extracellular matrix material has been removed.

21. The fasciculated nerve graft of claim 1, wherein about 95%, about 99%, or the entirety of the epineurial sheath has been removed.

22. A fasciculated nerve graft prepared according to a method comprising:
    treating a nerve tissue with one or more enzymes to at least partially degrade epineurial sheath and native extracellular matrix (ECM) material of the nerve tissue;
    washing the treated nerve tissue to remove the one or more enzymes and debris, thereby producing one or more nerve fascicles that are substantially free of epineurial sheath and native ECM material; and
    entubulating the one or more nerve fascicles in an entubulation material comprising a biocompatible material.

* * * * *

UNITED STATES PATENT AND TRADEMARK OFFICE
CERTIFICATE OF CORRECTION

PATENT NO. : 11,998,661 B2
APPLICATION NO. : 17/451489
DATED : June 4, 2024
INVENTOR(S) : Jennifer Faleris and Kasra Tajdaran It is certified that error appears in the above-identified patent and that said Letters Patent is hereby corrected as shown below:

In the Claims

In Column 15, Line 43, in Claim 7, before "graft of claim 1", delete "of".

In Column 16, Line 31, in Claim 18, before "50%", delete "about".

In Column 16, Line 31, in Claim 18, before "85%", delete "about".

In Column 16, Line 31, in Claim 18, before "95%", delete "about".

In Column 16, Line 32, in Claim 18, before "99%", delete "about".

In Column 16, Line 35, in Claim 19, before "95%", delete "about".

In Column 16, Line 35, in Claim 19, before "99%", delete "about".

Signed and Sealed this
Twenty-third Day of July, 2024

Katherine Kelly Vidal
*Director of the United States Patent and Trademark Office*